(12) United States Patent
Christine et al.

(10) Patent No.: US 7,175,590 B2
(45) Date of Patent: *Feb. 13, 2007

(54) APPARATUS FOR TRANS-CERVICAL ARTIFICIAL INSEMINATION AND EMBRYO TRANSFER

(75) Inventors: Robert R. Christine, Bethel, MO (US); Ricky A. Schoenbeck, Walworth, WI (US); Donald F. Hladky, Janesville, WI (US); Elton K. Feffer, Delavan, WI (US)

(73) Assignee: Continental Plastic Corp., Delavan, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/415,766

(22) PCT Filed: Nov. 1, 2001

(86) PCT No.: PCT/US01/44917

§ 371 (c)(1),
(2), (4) Date: Sep. 15, 2003

(87) PCT Pub. No.: WO02/35982

PCT Pub. Date: May 10, 2002

(65) Prior Publication Data

US 2004/0162461 A1 Aug. 19, 2004

(51) Int. Cl.
*A61B 17/43* (2006.01)
*A61D 7/00* (2006.01)
(52) U.S. Cl. ...................................... 600/35
(58) Field of Classification Search ............ 600/33–35; 604/55, 115, 176, 181, 191, 218, 264, 515, 604/906
See application file for complete search history.

(56) References Cited

U.S. PATENT DOCUMENTS 1,150,214 A 8/1915 London (Continued)

FOREIGN PATENT DOCUMENTS

EP 71538 2/1983

(Continued)

OTHER PUBLICATIONS

"*Reproduction Resources Artificial Breeding Equipment and Veterinary Supplies*", no date, pp. 1A, 1B, 1-17, 17A (admitted prior art).

(Continued)

*Primary Examiner*—John P. Lacyk
(74) *Attorney, Agent, or Firm*—Boyle Fredrickson Newholm Stein & Gratz, S.C.

(57) ABSTRACT

The invention relates to an apparatus and a method useful for non-surgical embryo transfer or artificial insemination of mammals. An apparatus for depositing media into the uterus of a mammal includes a conical chamber that has a plurality of perforations and flaps. An exterior spiral formation is configured for traversing or penetrating cervical passageway. A sheath having a frusto-conical rearward end extends axially from an aft end of the conical chamber. A tubular depositing chamber extends axially from the conical chamber to a position beyond a fore end of the conical chamber. Coupled to the rearward end of the depositing chamber is an embryo or semen packaging unit. The tubular depositing chamber has an end that has an aperture to permit the flow of semen out of the depositing chamber and into the uterus. The invention also involves a method employing the apparatus described.

52 Claims, 5 Drawing Sheets

U.S. PATENT DOCUMENTS

| | | |
|---|---|---|
| 3,467,101 A | 9/1969 | Fogarty et al. |
| 3,805,784 A | 4/1974 | Alter |
| 3,811,443 A | 5/1974 | Dickinson, IIi et al. |
| 3,910,275 A | 10/1975 | Babbey et al. |
| 4,192,294 A | 3/1980 | Vasilevsky et al. |
| 4,261,361 A | 4/1981 | Cassou |
| 4,318,414 A | 3/1982 | Schuster et al. |
| 4,453,936 A | 6/1984 | Cassou |
| 4,474,576 A | 10/1984 | Gobby |
| 4,642,094 A | 2/1987 | North, Jr. et al. |
| 4,832,681 A | 5/1989 | Lenck et al. |
| 4,846,785 A | 7/1989 | Cassou et al. |
| 4,865,589 A | 9/1989 | Simmet et al. |
| 5,084,004 A | 1/1992 | Ranoux |
| 5,147,315 A | 9/1992 | Weber |
| 5,374,247 A | 12/1994 | Lowery et al. |
| 5,464,409 A | 11/1995 | Mohajer |
| 5,472,419 A | 12/1995 | Bacich |
| 5,496,272 A | 3/1996 | Chung et al. |
| 5,536,243 A | 7/1996 | Jeyendran |
| 5,558,636 A | 9/1996 | Li et al. |
| 5,656,010 A | 8/1997 | Li et al. |
| 5,916,144 A | 6/1999 | Li et al. |
| 5,971,971 A | 10/1999 | Saint-Ramon et al. |
| 6,004,260 A | 12/1999 | Thompson |
| 2002/0072650 A1 | 6/2002 | Garcia et al. |
| 2002/0151765 A1 | 10/2002 | Pascual |

FOREIGN PATENT DOCUMENTS

| | | |
|---|---|---|
| EP | 189702 | 8/1986 |
| EP | 605406 | 7/1994 |
| FR | 1525336 | 9/1968 |
| FR | 2450102 | 3/1979 |
| FR | 2647668 | 6/1990 |
| FR | 2668054 | 10/1990 |
| FR | 2706124 | 8/1993 |
| FR | 2701385 | 8/1994 |
| FR | 2803189 | 6/2001 |
| GB | 2263642 | 8/1993 |
| JP | 6-154254 | 6/1994 |
| WO | 97/14365 | 4/1997 |
| WO | 01/49206 | 7/2001 |

OTHER PUBLICATIONS

Polge, C. et al. "Pregnancy Following Non-surgical Egg Transfer in Pigs", published in *The Veterinary Record*, Apr. 15, 1968.

Sims, M.M. et al., "Nonsurgical Embyro Transfer in Swine", published in the *Journal of Animal Science*, vol. 65, Supplement 1, pp. 386 (1987).

Reichenbach, H.D. et al., "Piglets Born After Transcervical Transfer of Embryos Into Recipient Gilts", *Veterinary Record*, 4 pages (1993).

Galvin, J.M. et al., "A Procedure for Successful Nonsurgical Embryo Transfer in Swine", pp. 1280-1289, (1994).

APPARATUS FOR TRANS-CERVICAL ARTIFICIAL INSEMINATION AND EMBRYO TRANSFER

CROSS-REFERENCE TO RELATED APPLICATIONS

This application claims priority based on U.S. Ser. No. 09/705,489 filed Nov. 3, 2000 now U.S. Pat. No. 6,511,415 and U.S. Provisional Patent Application No. 60/318,815 filed Sept. 7, 2001.

BACKGROUND OF THE INVENTION

1. Field of Invention

The present invention relates in general to the field of artificial insemination of mammals. More particularly, the present invention relates to an apparatus and a method useful for non-surgical embryo transfer and artificial insemination of mammals. Specifically, a preferred embodiment of the present invention relates to transfer of fluid medium comprising semen, a fluid medium containing embryos or some medicinal fluid into the uterus of a female mammal such as a sow.

2. Discussion of the Related Art

In recent years, effective application of artificial impregnation including artificial insemination and non-surgical embryo transfer has established a proven method for improving the production of domestic livestock. Generally, such techniques enhanced the ability to selectively breed a single genetically superior male for production traits with a large number of females. Selective breeding of course allows for livestock with improved genetic traits for production. Artificial insemination techniques also decrease the chance of diseases and physical injury that can be associated with the natural breeding process. As a result of these and other advantages, the use of artificial insemination and non-surgical embryo transfer have become a widespread technique in the management of many species of domestic livestock. One of the non-surgical embryo transfer systems described in the prior art, involves inserting a tubular instrument into the cervix of a recipient female, and then depositing 10–12 milliliters of liquid medium containing embryos into and through the instrument, the objective being to deposit the embryos in the uterus. However, other procedures have several drawbacks. First, there is no way to determine whether the instrument has been inserted far enough into the cervix so that its forward end is adjacent to the body of the uterus. As a result, instances where the forward end of the instrument remains lodged within the cervix, the embryos may never reach the uterus to initiate pregnancy, and thus pregnancy rate may be reduced. As a result of the aforementioned problems, the pregnancy rate or liter size in embryo-transfer may be reduced. This results in annual monetary losses due to the cost of maintaining the non-pregnant recipient animals.

Other conventional artificial insemination (AI) techniques in the industry for some species may result in reduced pregnancy rate or litter size because not enough sperm cells were deposited into the uterus. To compensate for this and to maximize pregnancy rate or liter size, larger numbers of sperm cells are introduced than may be necessary if the entire insemination dose was deposited into the uterus. This is also due to the difficulty associated with passing a conventional straight AI device through the cervix of some species. The reason the passageway of the cervix is difficult to navigate in most mammalian species is that the inside of the cervix has ridged folds of tissue which block straight entry. These folds need to be circumvented to penetrate the cervical passageway and reach the uterine body. Therefore, there is a need for an improved system for affecting the non-surgical transfer of embryos into recipient animals and artificial insemination, particularly those species having a cervix of the type, which is difficult to navigate, such as swine, sheep, and goats.

SUMMARY AND OBJECTIVES OF THE INVENTION

The present invention relates to an apparatus and a method useful for non-surgical impregnation of mammals. Specifically, a preferred embodiment for the present invention relates to transfer of fluid medium comprising semen or a fluid medium containing embryos into the uterus of an animal.

In accordance with one aspect of the invention, an apparatus for depositing semen into a uterus of a mammal includes a conical chamber that has a plurality of perforations. An exterior spiral formation of the chamber is configured for penetrating the spiral cervical passageway, which provides the entrance to the uterine body. A sheath having a frusto-conical rearward end extends axially from an aft end of the conical chamber. A fluid receptacle or semen or embryo packaging unit is coupled to a rearward end of the sheath. A tubular depositing chamber extends axially from the conical chamber to a position beyond a fore end of the conical chamber. The tubular depositing chamber has an end that has an aperture to permit the flow of semen or embryos out of the depositing chamber and into the uterus. An embryo or semen packaging unit is coupled to the rearward end of the depositing chamber.

In accordance with another aspect of the invention, a method of depositing semen or embryos into the uterus of a mammal includes the steps of: a) inserting a conical chamber having a fore end and an exterior spiral formation into cervix of a mammal, b) securing the conical chamber within walls of the cervix, c) projecting a depositing chamber through an interior portion of the conical chamber, d) moving the depositing chamber transcervically to a semen or embryo release position for release of semen or embryos in the uterus, and e) securing a semen or embryo packaging unit to the depositing member to deposit semen or embryos in the uterus.

Another benefit of the present invention is that for artificial insemination directly into the uterus of some species, the insemination time is reduced. Thus, labor costs are minimized. Still another benefit is that the device is inserted while the animal is standing so breeders can safely more quickly delivering the fluid to a multitude of animals and thus be more efficient.

These and other aspects and objects of the present invention will be better appreciated and understood when considered in conjunction with the following description and the accompanying drawings. It should be understood, however, that the following description, while indicating preferred embodiments of the present invention, is given by way of illustration and not of limitation. Many changes and modifications may be made within the scope of the present invention without departing from the spirit thereof, and the invention includes all such modifications.

BRIEF DESCRIPTION OF THE DRAWINGS

A clear conception of the advantages and features constituting the present invention, and of the construction and operation of typical mechanisms provided with the present invention, will become more readily apparent by referring to the exemplary, and therefore non-limiting, embodiments illustrated in the drawing accompanying and forming a part of this specification, wherein like reference numerals designate the same elements in the several views, and in which.

In describing the preferred embodiment of the invention, which is illustrated in the drawings, specific terminology will be resorted to for the sake of clarity. However, it is not intended that the invention be limited to the specific terms so selected and it is to be understood that each specific term includes a technical equivalents which operate in a similar manner to accomplish a similar purpose. For example, the word "connected" or terms similar thereto are often used. They are not limited to direct connection but include connection through other elements where such connection is recognized as being equivalent by those skilled in the art.

DETAILED DESCRIPTION OF PREFERRED EMBODIMENTS

1. Resume

The present invention and the various features and advantages details thereof are explained more fully with reference to the non-limiting embodiments described in detail in the following description.

Figure 1:
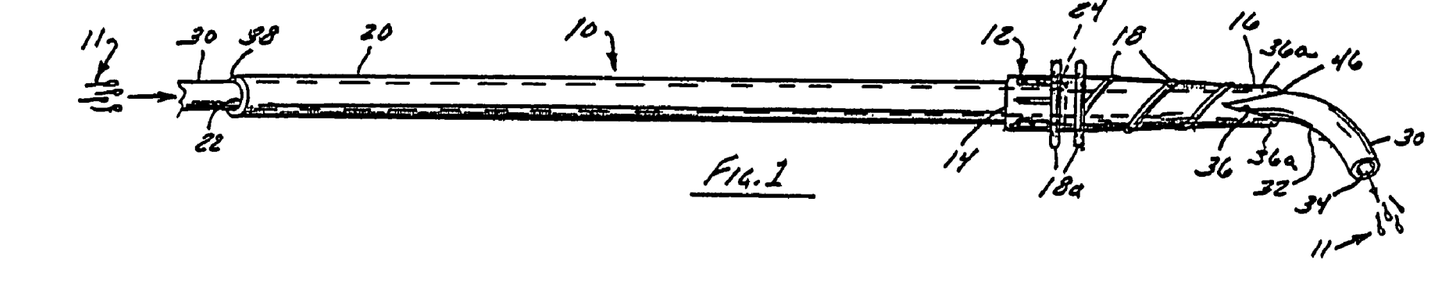
FIG. 1 is an elevation view of an apparatus for depositing a medium in a uterus in accordance with the present invention.

FIG. 1 shows an artificial insemination device or apparatus 10 and its components for depositing of semen or other medium 11 into a uterus of a mammal (not shown). The apparatus 10 comprises a sheath 20, a tubular depositing chamber 30, and a conical chamber 12 to be engaged with one another to transfer semen or other fluid medium from a receptacle or packaging unit 40 (FIG. 2) into the uterus of the mammal. The conical chamber 12 has a fore end 14, and an aft end 16, and an exterior spiral formation 18 configured for penetrating the passageway of a cervix. The fluid 11 could also contain live embryos or some medicine. Two circular sealing rings 18a provide a seal to prevent the fluid from leaking out of the cervix.

Figures 2, 3, 4:
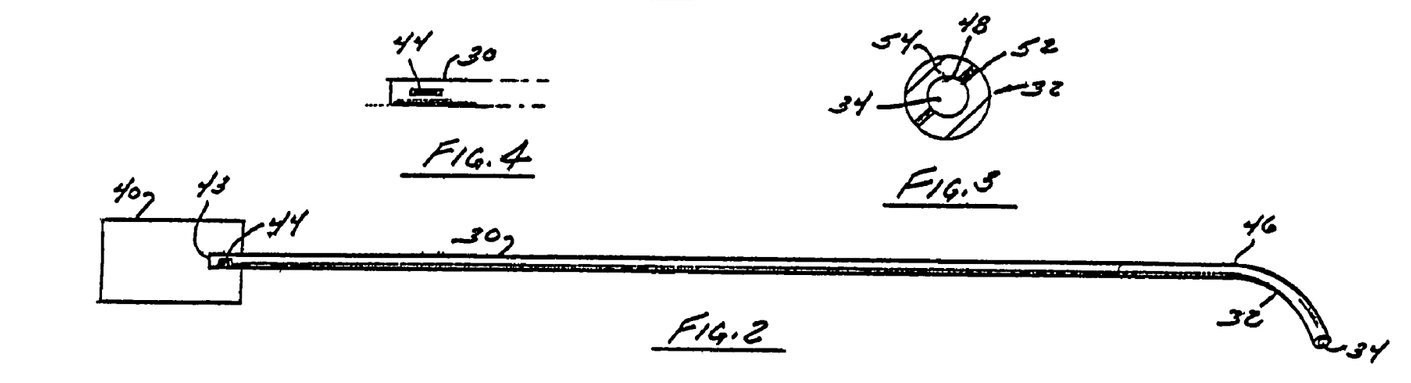
FIG. 2 corresponds to FIG. 1 and illustrates a tubular depositing chamber and or embryo or semen packaging unit in accordance with the present invention.
FIG. 3 is an end view of the tubular depositing chamber of FIG. 2 showing a raised curvilinear portion thereof.
FIG. 4 corresponds to FIG. 2 and illustrates a visual marker located on the tubular depositing chamber.

FIG. 2 shows the tubular depositing chamber 30 having an arcing end 32 for extending axially from the conical chamber 12 to a position beyond the fore end 16 of the conical chamber 12 as can be seen in FIG. 1. The arcing end 32 includes a flat portion 46 that is configured to abut a distal wall of the uterus to stop further insertion of the depositing chamber 30. As best seen in FIG. 1, the depositing chamber 30 is sized to be slidably inserted from arcing end 32 into the rear end 22 of the sheath 20. The length of tubular depositing chamber 30 is considerably longer than the sheath 20 so that, when fully inserted into the apparatus 10, the depositing chamber 30 projects beyond the forward end 24 of the sheath 20. By way of example, the sheath 20 may have an overall length of 21 inches (in.) and a diameter of 0.25 in. Preferably, the depositing chamber 30 has an overall length of 28 in. and a diameter of 0.09 in. These device dimensions are for an embodiment for a sow. Dimensions for other species will be different.

Figure 10A:
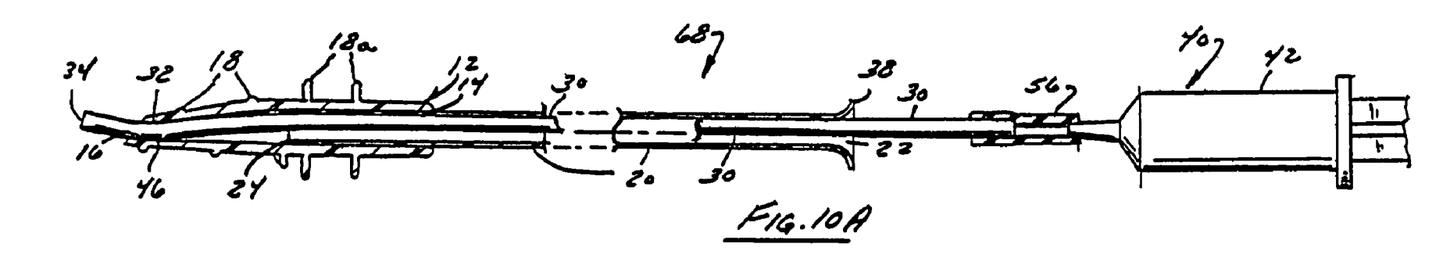
FIG. 10A corresponds to FIG. 1 being broken away to illustrate a first preferred embodiment of a complete artificial insemination device using a syringe.

An adapter 56 is connected to the rearward most end 43 of the depositing chamber 30 as shown in FIG. 10A. The adapter 56 may serve as a handle for the depositing chamber 30 because the adapter 56 may be grasped to manipulate the depositing chamber 30 by rotating it about the latitudinal axis and moving it forward and rearward relative to the sheath 20 inside the cervix.

FIG. 3 shows the arcing end 32 of the depositing chamber 30 has an aperture 34 with a raised curvilinear portion 54, which extends from an inner radius 48 to an outer radius 52. The surface of the portion 54 may be polished to smooth potentially rough edges.

As best viewed in FIG. 4, a visual marker 44 is located on the exterior surface of the depositing chamber 30 to indicate a relative orientation of the arcing end 32 of the depositing chamber 30.

Figure 5:
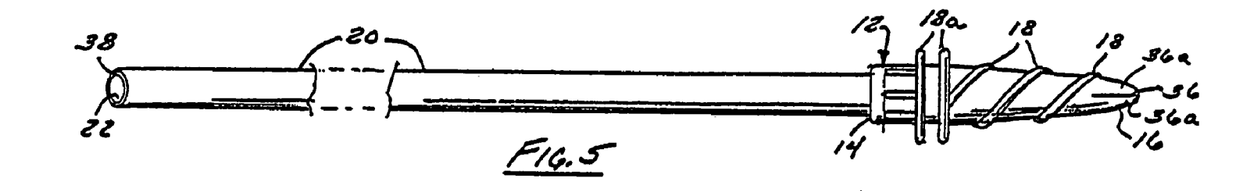
FIG. 5 corresponds to FIG. 1 and illustrates a sheath extending axially from an aft end of a conical chamber.
Figure 6:
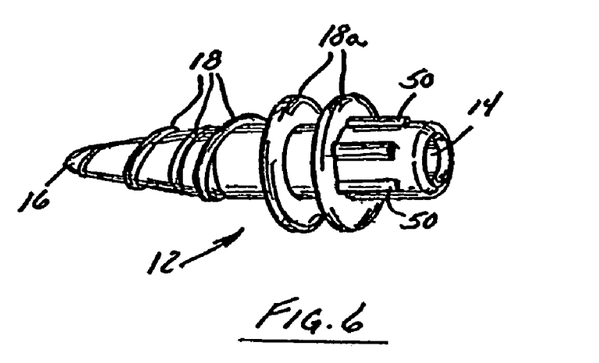
FIG. 6 corresponds to FIG. 1 and shows a perspective view of the conical chamber.
Figure 7:
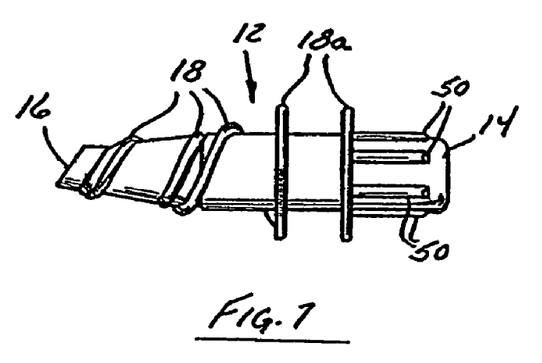
FIG. 7 is a plan view of the conical chamber.
Figure 8:
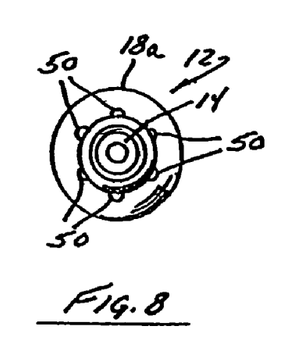
FIG. 8 is an end view of FIG. 7.

FIG. 5 shows a portion of the artificial insemination apparatus 10 in which the sheath 20 and the conical chamber 12 are engaged with one another. The conical chamber 12 includes aft and fore ends 14, 16 and the exterior spiral formation 18 is configured for penetrating the cervical passageway. The fore end 16 may be truncated as shown in FIG. 7. Alternatively, the aft end 14 of the conical chamber 12 may include a plurality of perforations 36 and flaps 36a extending laterally from the fore end 16 of the conical chamber 12 as best shown in FIG. 5. The flaps 36a are of sufficient length to encase the arcing end 32 of the depositing chamber 30 within an interior space of the conical chamber 12. The conical chamber 12 is preferably made of a flexible poly vinyl chloride (PVC) material. The exterior spiral formation 18 allows penetrating easily into the cervix of the mammal.

Figure 9A:
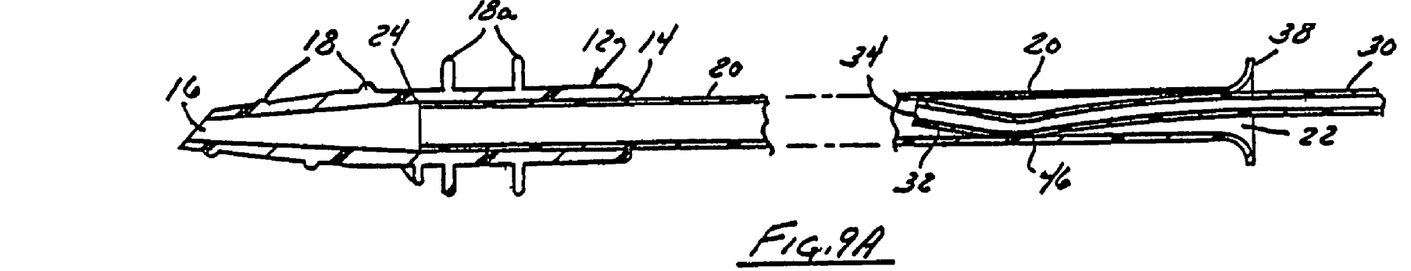
FIG. 9A corresponds to FIG. 1 with portions broken away to illustrate insertion of the tubular depositing chamber into the sheath.
Figure 9B:
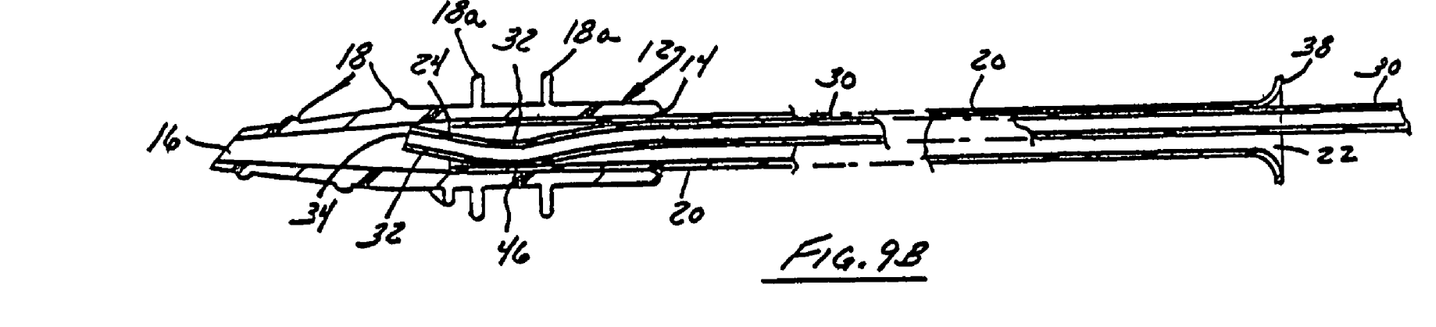
FIG. 9B corresponds to FIG. 9A and illustrates further insertion of the tubular depositing chamber into the sheath.
Figure 9C:
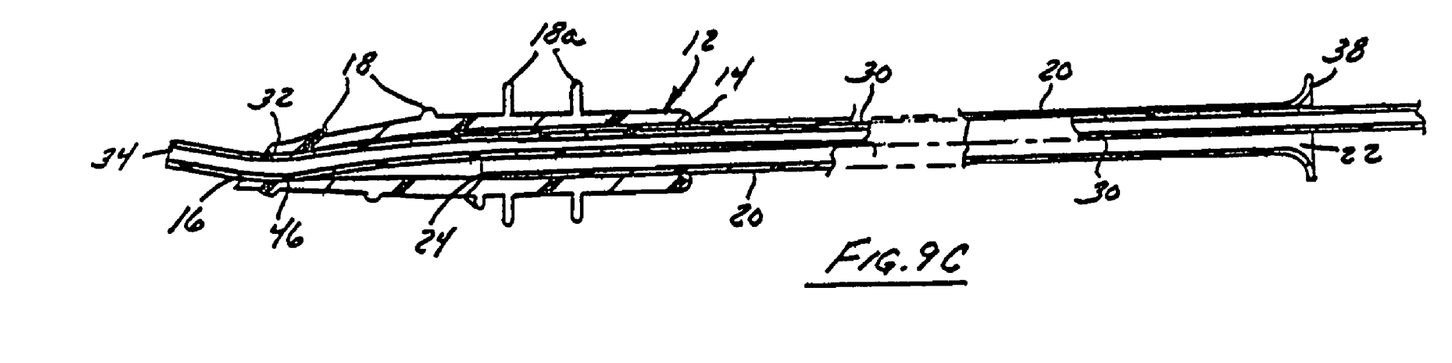
FIG. 9C corresponds to FIG. 9A and illustrates complete insertion of the tubular depositing chamber through the sheath.

As best shown in the embodiment of FIG. 7, the conical chamber 12 may have lands 50, which aid during assembly. The lands 50 also provide added friction for gloved hands when pushing inserting the apparatus 10 into the reproductive tract. FIGS. 9A through 9C illustrate the insertion of the tubular depositing chamber 30 into the sheath 20 of the artificial insemination apparatus 10. Referring to FIG. 9A, the arcing end 32 of the tubular depositing chamber is inserted into the rearward end 22 of the sheath 20 and travels through the sheath 20 until it reaches the conical chamber 12 that is connected (preferably by a friction fit or glued) to the forward end 24 of the sheath 20 as shown in FIGS. 9A–C. When the tubular depositing chamber 30 is pushed through the sheath 20, the arcing end 32 of the tubular depositing chamber 30 projects outside of the conical chamber 12 as best shown in FIG. 9C.

Figure 10B:
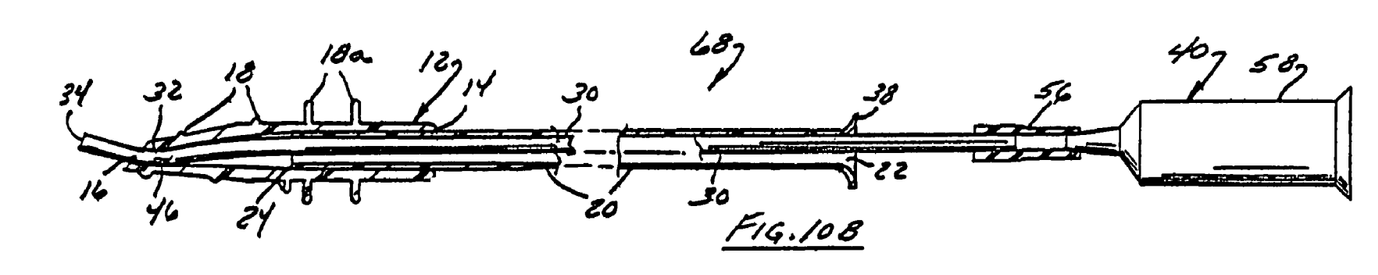
FIG. 10B corresponds to FIG. 1 being broken away to illustrate a second preferred embodiment of complete artificial insemination device using a semen packaging plastic tube.
Figure 10C:
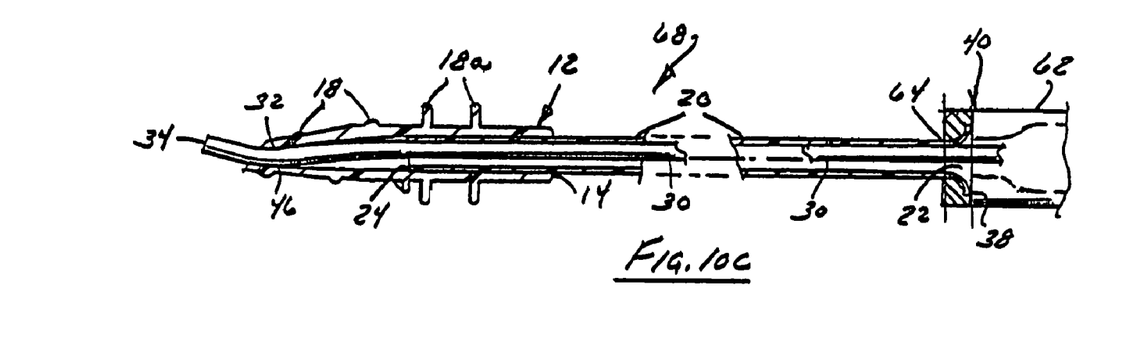
FIG. 10C corresponds to FIG. 1 being broken away to illustrate a third preferred embodiment of a complete artificial insemination device using a plastic bag.

FIGS. 10A through 10C illustrate the operation of the artificial insemination apparatus 10 using different containers or plastic embryo or semen packaging units. Specifically, FIG. 10A shows an apparatus 68 for depositing a medium 11 having the apparatus 10 in communication with a syringe 42. FIG. 10B shows an apparatus 68 having plastic semen packaging tube 58 such as a container which can be secured to adapter 56 for transferring semen or other media 11 into the depositing chamber 30. By moving the depositing chamber 30 to the semen release position, the medium 11 is discharged into the uterus.

FIG. 10C shows that the receptacle 40 may be a plastic bag 62, which has an opening 64 configured to communicate with the rearward end 22 of the depositing chamber 30 to transfer semen or other media to the uterus. The frustoconical shape 38 of the rear end 22 allows for a tight fitting of the plastic bag 62 to the apparatus 10.

The device 10 is preferably made of plastic materials. The chamber 12 is made up of a more flexible structure than the sheath 20 or the chamber 30. These materials are better than the stainless steel of prior art devices as they move efficiently and more effectively. The plastic devices can be more easily disposed after use or recycled. They are also more inexpensive to produce. Finally, the more flexible parts make the process more comfortable for the animals and as such there is no need to drug the animal.

Figure 11:
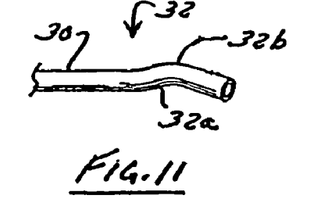
FIG. 11 shows another embodiment of the tubular depositing chamber.

As shown in FIG. 11, another embodiment has an arcing end 32 having a first bend 32a and a second bend 32b. This "double bend" structure can be used to better maneuver the depositing chamber 30 through the cervical cavity. This feature also reduces the space, from the left to the right extreme, the depositing chamber 30 would occupy in the cervix. Therefore, the "double bend" arcing end 32 will slip through the spiral conical chamber 12 easier and it should pass through the cervix easier, especially the cervix of gilts, which may be smaller and narrower.

Figure 12:
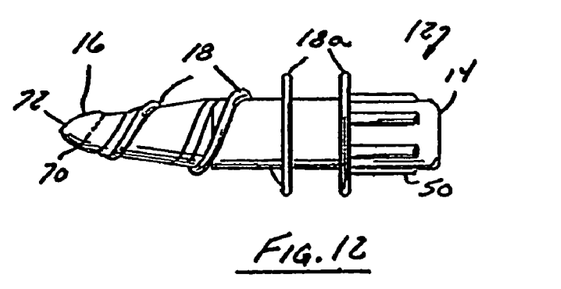
FIG. 12 shows yet another embodiment of the conical chamber

As shown in FIG. 12, in one embodiment the conical chamber 12 has a completely closed fore end 16 with at least one perforation 70. The end 16 may be completely sealed for added health and safety reasons such as for keeping the enclosed depositing chamber 30 in a sterile environment until it is ready for use. When ready, the operator will break through the perforated tip 72 and the sterile arcing end 32 of the depositing chamber 30 is then pushed past the perforated end 72 of the chamber 12 and through the cervix into the uterus. In one embodiment having multiple perforations, like the one shown in FIG. 5, the chamber 30 may be used to break through the perforations of the conical chamber 12. However, in that embodiment, perforations do not literally break away.

Referring to FIGS. 13–17, in these embodiments, the apparatus may consist of a sheath 20, an inner tubular depositing chamber 30, an outer chamber 80 having a fore end 82, an aft end 84, and a ribbed exterior formation 86 configured for traversing a passageway of a cervix. The ribbed configuration 86 is preferably comprised of two or more ribs 88 with grooves or lands 50 between the ribs. The sheath 20 has a forward end 24 and a rearward end (not shown) extending axially from the aft end 84 of the outer chamber 80. Specifically, the outer chamber 80 may be constructed of a soft, pliable foam having twin-tapered ends as shown.

The outer chamber 80 and the exterior ribbed formation 86 are dimensioned and configured for traversing the passageway of a cervix of a mammal, such as a sow. The outer chamber 80 has a wall with a smooth inner surface 81 and a ribbed outer surface 86. The outer chamber 80 is preferably affixed to the sheath 20 by an adhesive such as epoxy glue to prevent the outer chamber 80 from becoming disengaged while in the uterine tract. In one preferred embodiment the outer chamber 80 and sheath 20 are integrally molded from a single piece of plastic.

Figure 13:
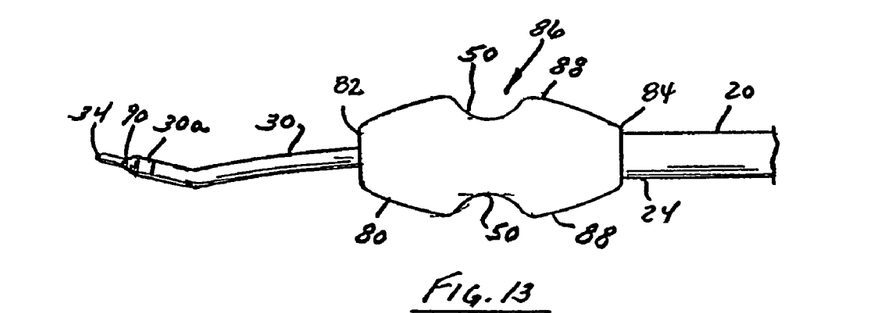
FIG. 13 is a side view of another embodiment of a device of the invention.
Figure 14:
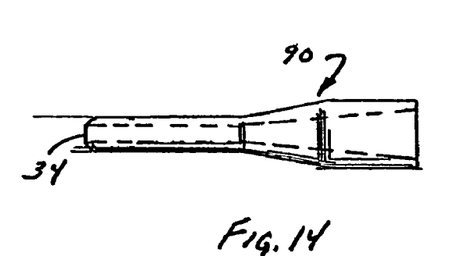
FIG. 14 is magnified side view of the tip of FIG. 13 showing the inner configuration is shadow.

The inner tubular depositing chamber 30 preferably has an end extending axially from the outer chamber 80 to a position beyond the fore end 82 of the outer chamber 80. The outmost end of the fore end 82 has an aperture 83. Preferably, the tubular depositing chamber 30 in this embodiment narrows in diameter from a rear end (not shown) to the aperture 34 at a front end 30a of the depositing chamber 30 as best shown in FIG. 14. As shown in the embodiment of FIG. 13, the depositing chamber front end 30a includes a tip 90 integral with the depositing chamber 30. In this embodiment, the tip 90 is attached to the bent depositing tubular chamber 30 as shown.

Figure 15:
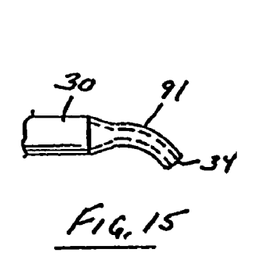
FIG. 15 is a magnified side view of another embodiment showing a arched tip configuration.
Figure 16:
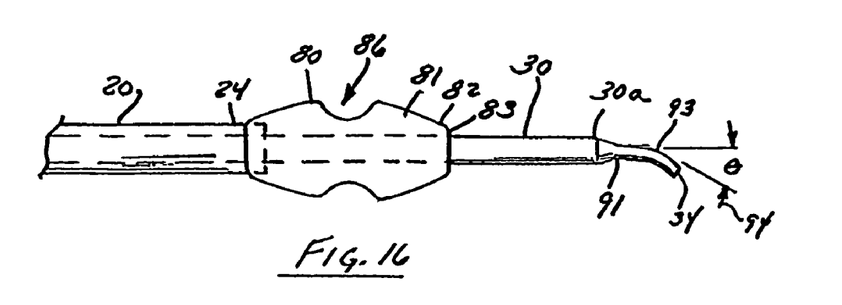
FIG. 16 is a side view of another embodiment of a device of the invention showing the inner configuration of the device in shadow.

In one embodiment best shown in FIGS. 15 and 16, the tip 90 is an arched tip 91 is preferably constructed of a hard plastic. An outside diameter of the tip is preferably narrow enough for the successful transcervical insemination of a gilt while the diameter of the aperture 34 therethrough is wide enough to allow unencumbered passage of boar semen. The arched tip 91 may be a single bend 93 in one embodiment (as shown) or multiple bends in other embodiments. In this embodiment, the depositing tubular chamber is preferably straight although it is foreseeable that a bent depositing chamber 30 would be desirable in combination with an arched tip 91 to give the combination a double bend configuration.

In the embodiment shown in FIGS. 15 and 16, the tip 90 is permanently bent at an angle 94 less than 45 degrees from a central axis 95 of the outer chamber 80. In the preferred embodiment, the angle 94 is between 18 and 30 degrees from the central axis 95. If arc is greater than 45 degrees, it is difficult to pass the device through the uterus of a gilt. The arched tip 91 is rigid and preferably has a polished end to prevent it from cutting the uterine wall lining. The arched tip 91 may also have a separate, rounded end which is also preferably smooth. The tip 90 is preferably a distinct member and is affixed to the inner tube 30 by an adhesive.

The inner depositing chamber 30 may be constructed of a flexible plastic such as polyethylene while the rigid arched tip 91 may be constructed from polyvinyl chloride or a high density, more rigid polyethylene.

While the arched tip 91 may constitute a separate member affixed to the inner tube 30, in one preferred embodiment the tip 90 is completely integral with the inner tube 30 and may be molded from a singular piece of extruded tubing. The tip 90 in this embodiment may also have an aperture 34 therethrough with a gradually narrowing frusto-conical inside diameter relative to the rear end of the tubular chamber 30 as best shown in FIG. 15.

2. In Use and Operation

When the device is in use with mammals, it can be used to deposit semen, embryos, medicines or other fluids. The animal need not be sedated and can remain standing during the depositing process unlike during most prior art methods. Specifically, the method of depositing fluid into a mammal includes inserting the forward end of the apparatus 10 (i.e. the conical chamber 12) first into a cervix of a uterus of a mammal. The conical-shaped chamber 12 is manipulated through the cervix by turning the connected sheath 20 about an axis and working the apparatus 10 toward the uterus.

This process is made easier by the screw-like, exterior spiral formation 18 of the conical chamber 12. The spiral exterior 18 also helps the operator stimulate the animal on the way to the uterus. Once the conical chamber 12 is in the uterus, it is secured within walls of the cervix by a slight rearward tug of the sheath 20 by the operator. Once secured by the operator, the depositing member or chamber 30 having the arcing end 32 is inserted through the sheath 20. The arcing end 32 is pushed inwardly until it passes through an interior portion of the conical chamber 12. Once the arcing end 32 passes out the depositing chamber 30, it is moved along until the operator experiences substantial resistance to further movement. In one embodiment, the operator can more easily determine the location of this release position by referencing a mark that appears on the shaft of the depositing chamber 30.

Once the operator reaches the fluid release position, a fluid receptacle 40 containing semen or other fluid is then attached to the rear end of depositing member 30. The operator lifts the attached receptacle 40 to a point where gravity helps the fluid move downward into the cavity of the depositing chamber 30 and past the conical chamber 12 to deposit the semen or fluid into the uterus.

The individual components described herein need not necessarily be formed in the disclosed shapes, or assembled in the disclosed configuration, but could be provided in virtually any shape, and assembled in virtually any configuration. For example, although the sheath and tubular depositing chamber could be used separately with minor success, combining them increases the ability to transverse the cervical passageway to the uterus.

Further, although the conical chamber is described herein as a physically separate module, it is apparent that it may be more fully integrated into the sheath. Furthermore, all disclosed features of each disclosed embodiment could be combined with, or substituted for, the disclosed features of every other disclosed embodiment except where such features are mutually exclusive. It is intended that the appended claims cover all such additions, modifications and rearrangements. Expedient embodiments of the present invention are differentiated by the appended sub claims.

What is claimed is:

1. An apparatus for depositing media into a uterus of a mammal, comprising:

a conical chamber having a fore end, an aft end, and an exterior spiral formation configured for traversing the passageway of a cervix;

a sheath having a forward end and a rearward end extending axially from the aft end of the conical chamber; and a tubular depositing chamber having an arcing end extending axially from the conical chamber to a position beyond the forward end of the sheath, wherein the arcing end has an aperture at its fore end and wherein the arcing end has a sufficient bend to enable the arcing end to gently engage a distal wall of the uterus and prevent perforation of the cervix by the tubular depositing chamber.

2. The apparatus of claim 1, wherein the fore end of the conical chamber comprises a plurality of perforations, which extend laterally toward the fore end of the conical chamber, and are adapted to be of sufficient length to encase the arcing end of the depositing chamber within the conical chamber.

3. The apparatus of claim 2, wherein the conical chamber is comprised of a flexible poly vinyl chloride (PVC) material.

4. The apparatus of claim 1 further comprising a fluid receptacle attached to the rearward end of the sheath and wherein the rearward end of the sheath further comprises a frusto-conical shape configured to be inserted into the receptacle.

5. The apparatus of claim 1, wherein the depositing chamber has a visual marker situated on an exterior surface of the depositing chamber to indicate a relative orientation of the arcing end of the depositing chamber.

6. The apparatus of claim 1, wherein the arcing end of the depositing chamber further comprises a flat portion, the flat portion configured to abut a distal wall of the uterus.

7. The apparatus of claim 1, wherein the aperture of the arcing member has an inner radius and an outer radius; and further comprising an adapter connected to the rearward most end of the depositing chamber.

8. The apparatus of claim 7 further comprising a raised curvilinear portion extending from the inner radius to the outer radius; and wherein a surface of the portion is polished smooth.

9. An apparatus for artificially impregnating a mammal, comprising:

a conical chamber including an exterior formation configured to fit into the cervical passageway;

a sheath having a frusto-conical rearward end extending axially from an aft end of the conical chamber;

a tubular depositing chamber having an arcing end for extending axially from the conical chamber to a position beyond a fore end of the conical chamber, the arcing end forming a double bend and an aperture to permit the flow of semen out of the depositing chamber and into the uterus, wherein the aperture has an inner radius and an outer radius and wherein the arcing end has a sufficient curvature or angle to enable the arcing end to gently engage a distal wall of the mammal; and an embryo or semen packaging unit coupled to the depositing chamber at the rearward end of the sheath.

10. The apparatus of claim 9, wherein a plurality of perforations extend laterally from the forward end of the conical chamber within an interior space of the conical chamber.

11. The apparatus of claim 9, wherein the conical chamber is comprised of a flexible poly vinyl chloride (PVC) material.

12. The apparatus of claim 9, further comprising a raised curvilinear portion extending from the inner radius to the outer radius.

13. The apparatus of claim 9, wherein the depositing chamber has a visual marker situated on the exterior surface of the depositing chamber.

14. A method for depositing semen or embryos into a uterus of a mammal comprising the steps of:
inserting a conical chamber having an exterior spiral formation into a cervix of a uterus of a mammal;
securing the chamber within the cervical passageway;
projecting a depositing chamber through an interior portion of the conical chamber;
moving the depositing chamber to a semen or embryo release position for release of semen or embryos in the uterus, wherein the step of securing the chamber within the cervical passageway further comprises sealing the conical chamber against the cervical passageway to prevent fluid loss through the passageway; and
securing an embryo or semen packaging unit to the depositing chamber; and
depositing embryos or semen in the uterus.

15. The method of claim 14 further comprising the step of moving the conical chamber to a position where there is substantial resistance to further movement.

16. The method of claim 15 further comprising the step of advancing the depositing chamber through the conical chamber to the semen release position for release of the semen in the uterus by breaking through perforations in the conical chamber.

17. The method of claim 16, wherein the step of advancing the depositing chamber further comprises the step of rotating the depositing chamber around an axis to traverse the cervical passageway.

18. The method of claim 17 further comprising the step of orienting the depositing chambers for proper release of the embryos or semen in the uterus.

19. The method of claim 18, wherein the step of orienting the depositing chamber for proper release is accomplished by verifying the projection of the arcing end using a mark on the exterior surface of the rear end of the depositing chamber.

20. A method for depositing of embryos or semen into a uterus comprising the steps of:
inserting a depositing chamber through an end of a conical chamber;
recessing an arcing fore end of the depositing chamber in an interior of the conical chamber;
inserting the conical chamber into the cervix;
securing the conical chamber in the cervix;
projecting the depositing chamber through the interior portion of the conical chamber;
moving the depositing chamber to an embryo or semen release position for release of embryos or semen in the uterus;
securing an embryo or semen packaging unit to a depositing chamber; and
depositing embryos or semen in the uterus wherein the step of securing the conical chamber in the cervix further comprises sealing the conical chamber within the cervix to prevent fluid loss through the cervix.

21. The method of claim 20 further comprising the step of moving the conical chamber to a position where there is substantial resistance to further forward movement.

22. The method of claim 20 further comprising the step of advancing the depositing chamber through the conical chamber to the embryo or semen release position for release of embryos or semen in the uterus.

23. The method of claim 20, wherein the step of advancing the depositing chamber further comprises the step of rotating the depositing chamber about the latitudinal axis to transverse the cervical passageway.

24. The method of claim 23 further comprising the step of orienting the depositing chamber for proper release of embryos or semen in the uterus.

25. The method of claim 24, wherein the step of orienting the depositing chamber for proper release comprises the step of verifying that the end of the depositing chamber is projecting downwardly by properly positioning a mark on the exterior surface of the rear end of the depositing chamber.

26. An apparatus for depositing media into a uterus of a mammal, comprising:
an outer chamber having a fore end, an aft end, and a ribbed exterior formation configured for traversing a passageway of a cervix;
a sheath having a forward end and a rearward end extending axially from the aft end of the chamber; and
a tubular depositing chamber having an end extending axially from the outer chamber to a position beyond the fore end of the outer chamber, wherein the end has an aperture at a fore end and wherein the end is sufficiently curved or angled with respect to the longitudinal axis of the tubular depositing chamber to enable the end to gently engage a distal wall of the uterus and to avoid perforating it.

27. The apparatus of claim 26, wherein the tubular depositing chamber narrows in diameter from the aft end to the aperture at the fore end of the depositing chamber.

28. The apparatus of claim 27, wherein the end of the tubular depositing chamber comprises an arched tip integral with the depositing chamber.

29. The apparatus of claim 28, wherein the arched tip has an outside diameter that is narrow enough for the successful transcervical insemination of a gilt while the inner diameter is wide enough to allow unencumbered passage of boar semen.

30. The apparatus of claim 29, wherein the arched tip has a single bend.

31. The apparatus of claim 29, wherein the arched tip has multiple bends.

32. The apparatus of claim 30, wherein the bend arches at an angle between 18 and 30 degrees from a central axis of the outer chamber.

33. The apparatus of claim 30, wherein the bend arches at an angle less than 45 degrees from a central axis of the outer chamber.

34. An apparatus for depositing media into a uterus of a mammal comprising:
a chamber having a fore end, an aft end, and an exterior ribbed formation configured for traversing the passageway of a cervix of a mammal;
a sheath having a forward end and a rearward end, wherein the sheath extends axially from the aft end of the chamber; and
a flexible inner tube within the sheath comprising an arched tip having an aperture at an outermost end, wherein the arched tip sufficiently curves with respect to the longitudinal axis of the flexible inner tube to enable the arched tip to gently engage a distal wall of the uterus.

35. The apparatus of claim 34, wherein the arched tip is rigid.

36. The apparatus of claim 35, wherein the arched tip has a polished end.

37. The apparatus of claim 35, wherein the arched tip has a rounded end.

38. The apparatus of claim 35, wherein the arched tip has a smooth end.

39. The apparatus of claim 35, wherein the arched tip constitutes a separate member affixed to the inner tube.

40. The apparatus of claim 35, wherein the chamber has a wall with a smooth inner surface and a ribbed outer surface.

41. The apparatus of claim 39, wherein the chamber and sheath are integral.

42. A flexible inner tube for use with an artificial insemination device comprising a rigid arched tip, arching at an angle between 18 and 30 degrees of the central axis, having an aperture at an outermost end, and integral with the inner tube.

43. An apparatus for depositing media into a uterus of a mammal, comprising
   a bent tip having an aperture therethrough with a first diameter; and
   an inner tube having an aperture with a second, larger diameter, wherein both the tip and the tube are constructed from a single extruded tube and wherein the tip has a sufficient bend to enable the tip to gently engage a distal wall of the uterus and to prevent perforation through the uterus wall.

44. The apparatus of claim 26, wherein the tip is integral with the inner tube.

45. The method of claim 20 further comprising the step of moving the conical chamber to a position where there is substantial resistance to further movement.

46. The apparatus of claim 26, wherein attached upon the end of the tubular depositing chamber is a straight tip having an aperture within with a gradually decreasing inside diameter, and said tip is integral with the depositing chamber.

47. The apparatus of claim 26, wherein the outside chamber is comprised of a foam, twin-tapered material.

48. The apparatus of claim 1 wherein the arcing end deviates from the longitudinal axis of the tubular depositing chamber an angular distance of between 10 degrees and 45 degrees.

49. The apparatus of claim 48 wherein the arcing end deviates from the longitudinal axis of the tubular depositing chamber or angular distance of between 18 and 30 degrees.

50. The apparatus of claim 1 wherein the conical chamber includes at least one sealing member engageable with the cervix of the mammal to prevent fluid from leaking out of the cervix.

51. The apparatus of claim 50 wherein the at least one sealing member extends at least partially radially outwardly from the conical chamber.

52. The apparatus of claim 50 wherein the conical chamber includes a pair of sealing members extending outwardly from the conical chamber and separated by a groove.

* * * * *